(12) United States Patent
Wyss et al.

(10) Patent No.: US 8,764,841 B2
(45) Date of Patent: Jul. 1, 2014

(54) MOBILE BEARING ASSEMBLY HAVING A CLOSED TRACK

(75) Inventors: Joseph G. Wyss, Fort Wayne, IN (US); Jordan S. Lee, Warsaw, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 218 days.

(21) Appl. No.: 12/049,750

(22) Filed: Mar. 17, 2008

(65) Prior Publication Data

US 2008/0243261 A1    Oct. 2, 2008

Related U.S. Application Data

(60) Provisional application No. 60/909,126, filed on Mar. 30, 2007.

(51) Int. Cl.
     *A61F 2/38*          (2006.01)

(52) U.S. Cl.
     USPC ................................ 623/20.33; 623/20.32

(58) Field of Classification Search
     USPC .......................................... 623/20.14–20.36
     See application file for complete search history.

(56) References Cited

U.S. PATENT DOCUMENTS

| | | |
|---|---|---|
| 3,506,982 A | 4/1970 | Steffee |
| 3,605,123 A | 9/1971 | Hahn |
| 3,855,638 A | 12/1974 | Pilliar |
| 3,906,550 A | 9/1975 | Rostoker et al. |
| 3,953,899 A | 5/1976 | Charnley |
| 4,016,606 A | 4/1977 | Murray et al. |
| 4,205,400 A | 6/1980 | Shen et al. |
| 4,207,627 A | 6/1980 | Cloutier |
| 4,213,816 A | 7/1980 | Morris |
| 4,216,549 A * | 8/1980 | Hillberry et al. ........... 623/20.26 |
| 4,224,696 A | 9/1980 | Murray et al. |
| 4,224,697 A | 9/1980 | Murray |
| 4,340,978 A | 7/1982 | Buechel et al. |
| 4,454,612 A | 6/1984 | McDaniel et al. |
| 4,470,158 A | 9/1984 | Pappas et al. |
| 4,479,271 A | 10/1984 | Bolesky |
| 4,501,031 A | 2/1985 | McDaniel et al. |
| 4,568,348 A | 2/1986 | Johnson et al. |
| 4,589,883 A | 5/1986 | Kenna |
| 4,636,219 A | 1/1987 | Pratt et al. |

(Continued)

FOREIGN PATENT DOCUMENTS

| | | |
|---|---|---|
| BE | 1008201 | 2/1996 |
| DE | 10012060 | 9/2001 |

(Continued)

OTHER PUBLICATIONS

"The Oxford Partial Knee", Biomet Patients and Caregivers-Joint Replacement, www.biomet.com/patients/oxford.cfm, Biomet, Inc. 2008, 3 pages.

(Continued)

*Primary Examiner* — David Isabella
*Assistant Examiner* — Jacqueline Woznicki
(74) *Attorney, Agent, or Firm* — Barnes & Thornburg LLP

(57) ABSTRACT

A mobile tibial assembly includes a tibial tray and a tibial insert. The tibial tray includes a closed track. The tibial insert includes a stem configured to be inserted into the closed track and retained therein. The tibial insert is movable along the closed track once inserted.

21 Claims, 12 Drawing Sheets

(56) References Cited

U.S. PATENT DOCUMENTS

| | | | |
|---|---|---|---|
| 4,718,413 A | 1/1988 | Johnson | |
| 4,719,908 A | 1/1988 | Averill et al. | |
| 4,728,332 A | 3/1988 | Albrektsson | |
| 4,743,261 A | 5/1988 | Epinette | |
| 4,795,468 A | 1/1989 | Hodorek et al. | |
| 4,911,721 A | 3/1990 | Branemark et al. | |
| 4,936,847 A | 6/1990 | Manginelli | |
| 4,944,757 A | 7/1990 | Martinez et al. | |
| 4,950,298 A | 8/1990 | Gustilo et al. | |
| 4,997,445 A | 3/1991 | Hodorek | |
| 5,019,103 A | 5/1991 | Van Zile et al. | |
| 5,047,058 A | 9/1991 | Roberts et al. | |
| 5,108,452 A | 4/1992 | DeMane et al. | |
| 5,152,797 A | 10/1992 | Luckman et al. | |
| 5,201,769 A | 4/1993 | Schutzer | |
| 5,226,915 A | 7/1993 | Bertin | |
| 5,263,987 A | 11/1993 | Shah | |
| 5,282,868 A | 2/1994 | Bahler | |
| 5,330,532 A | 7/1994 | Ranawat | |
| D354,810 S | 1/1995 | Nazre | |
| 5,395,401 A * | 3/1995 | Bahler | 623/20.29 |
| D357,534 S | 4/1995 | Hayes | |
| D359,557 S | 6/1995 | Hayes | |
| 5,458,637 A | 10/1995 | Hayes | |
| 5,609,639 A * | 3/1997 | Walker | 623/20.29 |
| 5,609,640 A | 3/1997 | Johnson | |
| 5,658,341 A | 8/1997 | Delfosse | |
| 5,702,458 A | 12/1997 | Burstein et al. | |
| 5,702,459 A | 12/1997 | Hummer et al. | |
| 5,716,361 A | 2/1998 | Masini | |
| 5,755,801 A * | 5/1998 | Walker et al. | 623/20.21 |
| 5,800,560 A | 9/1998 | Draenert | |
| 5,810,827 A | 9/1998 | Haines et al. | |
| 5,824,106 A | 10/1998 | Fournol | |
| 5,855,296 A | 1/1999 | McCann et al. | |
| 5,871,541 A | 2/1999 | Gerber | |
| 5,879,354 A | 3/1999 | Haines et al. | |
| 5,888,034 A | 3/1999 | Greenberg | |
| 5,944,722 A | 8/1999 | Masini | |
| 5,947,973 A | 9/1999 | Masini | |
| 5,957,926 A | 9/1999 | Masini | |
| 5,957,979 A | 9/1999 | Beckman et al. | |
| 5,961,523 A | 10/1999 | Masini | |
| 5,971,989 A | 10/1999 | Masini | |
| 6,004,351 A | 12/1999 | Tomita et al. | |
| 6,010,534 A * | 1/2000 | O'Neil et al. | 623/20.34 |
| 6,019,767 A | 2/2000 | Howell | |
| 6,039,764 A * | 3/2000 | Pottenger et al. | 623/20.32 |
| 6,056,754 A | 5/2000 | Haines et al. | |
| 6,068,633 A | 5/2000 | Masini | |
| 6,077,269 A | 6/2000 | Masini | |
| 6,102,916 A | 8/2000 | Masini | |
| 6,106,529 A | 8/2000 | Techiera | |
| 6,123,728 A | 9/2000 | Brosnahan et al. | |
| 6,139,581 A | 10/2000 | Engh et al. | |
| 6,171,340 B1 | 1/2001 | McDowell | |
| 6,187,010 B1 | 2/2001 | Masini | |
| 6,197,064 B1 | 3/2001 | Haines et al. | |
| 6,214,011 B1 | 4/2001 | Masini | |
| 6,254,604 B1 | 7/2001 | Howell | |
| 6,254,605 B1 | 7/2001 | Howell | |
| 6,296,666 B1 * | 10/2001 | Gardner | 623/20.29 |
| 6,361,564 B1 * | 3/2002 | Marceaux et al. | 623/20.29 |
| 6,419,707 B1 | 7/2002 | Leclercq | |
| 6,428,577 B1 | 8/2002 | Evans et al. | |
| 6,494,914 B2 | 12/2002 | Brown et al. | |
| 6,503,254 B2 | 1/2003 | Masini | |
| 6,506,215 B1 | 1/2003 | Letot et al. | |
| 6,520,964 B2 | 2/2003 | Tallarida et al. | |
| 6,602,292 B2 * | 8/2003 | Burkinshaw | 623/20.2 |
| 6,616,696 B1 | 9/2003 | Merchant | |
| 6,660,039 B1 * | 12/2003 | Evans et al. | 623/20.29 |
| 6,702,821 B2 | 3/2004 | Bonutti | |
| 6,730,128 B2 | 5/2004 | Burstein | |
| 6,770,078 B2 | 8/2004 | Bonutti | |
| 6,869,448 B2 | 3/2005 | Tuke et al. | |
| 6,916,341 B2 | 7/2005 | Rolston | |
| 6,946,001 B2 | 9/2005 | Sanford et al. | |
| 7,033,397 B2 | 4/2006 | Webster et al. | |
| 7,101,401 B2 * | 9/2006 | Brack | 623/20.33 |
| 7,105,027 B2 | 9/2006 | Lipman et al. | |
| 7,115,131 B2 | 10/2006 | Engh et al. | |
| 7,708,741 B1 | 5/2010 | Bonutti | |
| 7,931,690 B1 | 4/2011 | Bonutti | |
| 2001/0037155 A1 | 11/2001 | Merchant | |
| 2002/0055784 A1 | 5/2002 | Burstein et al. | |
| 2003/0009232 A1 | 1/2003 | Metzger et al. | |
| 2003/0028196 A1 | 2/2003 | Bonutti | |
| 2003/0033018 A1 | 2/2003 | Merchant | |
| 2003/0120346 A1 | 6/2003 | Mercinek et al. | |
| 2003/0158606 A1 | 8/2003 | Coon et al. | |
| 2003/0181984 A1 | 9/2003 | Abendschein | |
| 2003/0187510 A1 | 10/2003 | Hyde | |
| 2003/0195633 A1 | 10/2003 | Hyde | |
| 2004/0006394 A1 | 1/2004 | Lipman et al. | |
| 2004/0039447 A1 | 2/2004 | Simon et al. | |
| 2004/0107000 A1 | 6/2004 | Felt et al. | |
| 2004/0143338 A1 | 7/2004 | Burkinshaw et al. | |
| 2004/0153066 A1 | 8/2004 | Coon et al. | |
| 2004/0153164 A1 | 8/2004 | Sanford et al. | |
| 2004/0167630 A1 | 8/2004 | Rolston | |
| 2004/0193280 A1 | 9/2004 | Webster et al. | |
| 2004/0254645 A1 | 12/2004 | Arnin et al. | |
| 2005/0015153 A1 * | 1/2005 | Goble et al. | 623/23.46 |
| 2005/0027365 A1 | 2/2005 | Burstein et al. | |
| 2005/0096747 A1 | 5/2005 | Tuttle et al. | |
| 2005/0119663 A1 | 6/2005 | Keyer et al. | |
| 2005/0119664 A1 | 6/2005 | Carignan et al. | |
| 2005/0143830 A1 | 6/2005 | Marcinek et al. | |
| 2005/0143831 A1 * | 6/2005 | Justin et al. | 623/20.17 |
| 2005/0143833 A1 | 6/2005 | Merchant | |
| 2005/0149041 A1 | 7/2005 | McGinley et al. | |
| 2005/0171604 A1 | 8/2005 | Michalow | |
| 2005/0171612 A1 | 8/2005 | Rolston | |
| 2005/0177242 A1 | 8/2005 | Lotke | |
| 2005/0197709 A1 | 9/2005 | Schaefer et al. | |
| 2005/0203384 A1 | 9/2005 | Sati et al. | |
| 2005/0234465 A1 | 10/2005 | McCombs et al. | |
| 2005/0240273 A1 | 10/2005 | Khandkar et al. | |
| 2005/0278034 A1 | 12/2005 | Johnson et al. | |
| 2006/0004460 A1 | 1/2006 | Engh et al. | |
| 2006/0009776 A1 | 1/2006 | Justin et al. | |
| 2006/0009854 A1 | 1/2006 | Justin et al. | |
| 2006/0009855 A1 | 1/2006 | Goble et al. | |
| 2006/0030855 A1 | 2/2006 | Haines | |
| 2006/0030945 A1 | 2/2006 | Wright | |
| 2006/0085072 A1 | 4/2006 | Funk et al. | |
| 2006/0089720 A1 | 4/2006 | Schneier | |
| 2006/0122616 A1 | 6/2006 | Bennett et al. | |
| 2006/0129246 A1 | 6/2006 | Steffensmeier | |
| 2006/0190086 A1 | 8/2006 | Clemow | |
| 2006/0195195 A1 | 8/2006 | Burstein et al. | |
| 2006/0195196 A1 | 8/2006 | Pendleton et al. | |
| 2006/0235537 A1 | 10/2006 | Kuczynski et al. | |
| 2006/0265079 A1 | 11/2006 | D'Alessio | |
| 2007/0010890 A1 | 1/2007 | Collazo | |
| 2007/0100459 A1 | 5/2007 | Rhodes | |
| 2007/0100460 A1 | 5/2007 | Rhodes | |
| 2008/0033567 A1 * | 2/2008 | Stchur | 623/20.33 |
| 2008/0086210 A1 | 4/2008 | Fox | |

FOREIGN PATENT DOCUMENTS

| | | |
|---|---|---|
| DE | 10053623 | 5/2002 |
| EP | 0135319 A2 | 3/1985 |
| EP | 0183670 | 6/1986 |
| EP | 0327387 A2 | 8/1989 |
| EP | 0328463 A1 | 8/1989 |
| EP | 0874596 A1 | 11/1998 |
| EP | 0709075 B1 | 8/2001 |
| EP | 1327424 | 7/2003 |
| EP | 1329205 A1 | 7/2003 |
| EP | 1374782 A2 | 1/2004 |
| EP | 1442726 | 8/2004 |

(56) References Cited

FOREIGN PATENT DOCUMENTS

| EP | 1442728 | A2 | 8/2004 |
|---|---|---|---|
| EP | 1550418 | | 7/2005 |
| EP | 1557144 | A1 | 7/2005 |
| EP | 1584309 | | 10/2005 |
| EP | 1669034 | A1 | 6/2006 |
| EP | 1702590 | A2 | 9/2006 |
| EP | 1741412 | | 1/2007 |
| FR | 2663536 | | 12/1991 |
| FR | 2702369 | | 9/1994 |
| FR | 2721820 | | 1/1996 |
| FR | 2885516 | | 11/2006 |
| GB | 2355935 | | 5/2001 |
| JP | 2002272756 | A | 9/2002 |
| WO | 9110412 | A1 | 7/1991 |
| WO | 9524874 | A1 | 9/1995 |
| WO | 9716129 | A1 | 5/1997 |
| WO | 0013616 | A1 | 3/2000 |
| WO | 0170143 | A1 | 9/2001 |
| WO | 0209623 | | 2/2002 |
| WO | 03068119 | A2 | 8/2003 |
| WO | 2004001569 | A2 | 12/2003 |
| WO | 2005009298 | A1 | 2/2005 |
| WO | 2005025451 | A2 | 3/2005 |
| WO | 2005037065 | A2 | 4/2005 |
| WO | 2005044150 | A1 | 5/2005 |
| WO | 2005069957 | A2 | 8/2005 |
| WO | 2006074503 | A1 | 7/2006 |
| WO | 2006078511 | A1 | 7/2006 |
| WO | 2006078528 | A2 | 7/2006 |
| WO | 2006078864 | A1 | 7/2006 |
| WO | 2006106419 | A2 | 10/2006 |
| WO | 2006112911 | A2 | 10/2006 |

OTHER PUBLICATIONS

"Preservation Uni-compartmental Knee", DePuy Orthopaedics, Inc. 2002, 31 pages.

European Search Report for European Patent Application No. 08251211.2-2310, Jul. 21, 2008, 7 pgs.

European Search Report for European Patent Application No. 08251213.8-2310, Jul. 9, 2008, 7 pgs.

European Search Report for European Patent Application No. 08251210.4-2310, Jun. 20, 2008, 7 pgs.

European Search Report for European Patent Application No. 08251209.6-2310, Jul. 9, 2008, 7 pgs.

European Search Report for European Patent Application No. 08251212.0-2310, Jul. 21, 2008, 7 pgs.

Extended European Search Report for European Patent Application No. 10189881.5-2310, Feb. 17, 2011, 6 pgs.

Extended European Search Report for European Patent Application No. 10189885.6-2310, Mar. 18, 2011, 7 pgs.

Chinese First Office Action, Chinese Patent Application No. 200810128765.8, Aug. 15, 2011, 8 pages.

Chinese First Office Action, Chinese Patent Application No. 200810125845.8, Aug. 24, 2011, 7 pages.

\* cited by examiner

MOBILE BEARING ASSEMBLY HAVING A CLOSED TRACK

This patent application claims priority to and the benefit of U.S. Provisional Patent Application Ser. No. 60/909,126 entitled "Mobile Bearing Assembly Having A Closed Track" by Joseph G. Wyss et al., which was filed on Mar. 30, 2007, the entirety of which is expressly incorporated herein by reference.

Cross-reference is made to U.S. Utility patent application Ser. No. 12/049,753 entitled "MOBILE BEARING ASSEMBLY," which was filed on Mar. 17, 2008 by Jordan S. Lee et al., to U.S. Utility patent application Ser. No. 11/694,389 entitled "MOBILE BEARING ASSEMBLY HAVING OFFSET DWELL POINT," which was filed on Mar. 30, 2007 by Jordan S. Lee et al., to U.S. Utility patent application Ser. No. 12/049,759 entitled "MOBILE BEARING ASSEMBLY HAVING MULTIPLE ARTICULATION INTERFACES," which was filed on Mar. 17, 2008 by Jordan S. Lee et al., and to U.S. Utility patent application Ser. No. 12/049,699 entitled "MOBILE BEARING ASSEMBLY HAVING A NON PLANAR INTERFACE SURFACE," which was filed on Mar. 17, 2008 by Jordan S. Lee et al., the entirely entirety of all of which is expressly incorporated herein by reference.

TECHNICAL FIELD

The present disclosure relates generally to orthopaedic prostheses, and particularly to tibial assemblies including a tibial tray and a tibial insert.

BACKGROUND

During the lifetime of a patient, it may be necessary to perform a joint replacement procedure on the patient as a result of, for example, disease or trauma. For example, many knee replacement surgeries are performed each year. Total knee replacement or arthroplasty may involve replacement of the mid-shaft portion of the femur, proximal, distal, and/or total femur, and proximal tibia. Unicompartmental knee replacement or arthroplasty involves unicondylar resurfacing. Unicompartmental knee arthroplasty provides an alternative to total knee arthroplasty for rehabilitating knees when only one condyle has been damaged as a result of trauma or disease such as noninflammatory degenerate joint disease or its composite diagnosis of osteoarthritis or post-traumatic arthritis. As such, unicompartmental knee arthroplasty may be indicated for use in patients undergoing surgery for a severely painful and/or disabled joint damaged as a result of osteoarthritis, traumatic arthritis, rheumatoid arthritis, or a failed previous implant when only one condyle of the knee (medial or lateral) is affected. Further, unicompartmental knee replacements may be "multi-piece" replacements in which a unicompartmental tibial insert is used to replace each of the medial and lateral condyles of the patient. A single, total femoral component or two partial femoral components may be used to cooperate with the two unicompartmental inserts.

In addition, in some knee replacement procedures, a total knee tibial tray may used with a unicompartmental tibial insert. For example, a total knee tibial tray may be used with a single unicompartmental tibial insert to replace either the medial or lateral condyle of the patient's knee. Alternatively, a total knee tibial tray may be used with two unicompartmental tibial inserts, each replacing one of the medial and lateral condyles of the patient's knee. In such applications, the medial and lateral unicompartmental tibial inserts may have different characteristics and be selected based on the orthopaedic considerations associated with the respective condyle of the patient's knee.

Unicompartmental knee replacements are intended to provide increased patient mobility and reduce pain by replacing the damaged knee joint articulation in patients where there is evidence of sufficient sound bone to seat and support the components. Age and activity level factor into all reconstructive procedures and the state of the arthritis determines the treatment. With the advancement of minimally invasive techniques that support unicompartmental knee reconstruction, a growing number of patients are offered this alternative for relief from the disabling pain of arthritis and for the potential benefits of a rapid recovery.

A tibial assembly of a unicompartmental knee prosthesis typically includes a tibial tray configured to be coupled to the patient's tibia and a polymer tibial bearing or insert adjacent the tibial tray. As discussed above, the tibial tray may be a total or unicompartmental tibial tray. The tibial insert includes an upper bearing surface configured to engage a corresponding articulating condylar surface of a femoral component coupled to the patient's femur. A mobile tibial assembly generally refers to a tibial assembly wherein the tibial insert is movable relative to the tibial tray. In other words, the tibial insert may rotate relative to the tray and/or the tibial insert may move medially, laterally, anteriorly, and/or posteriorly relative to the tibial tray. This motion of the tibial insert relative to the tray may be constrained in any number of ways in order to limit the type of motion of the tibial insert. For example, the tibial insert may be limited to anterior/posterior motion relative to the tibial tray and/or rotation of the tibial insert relative to the tibial tray may be limited to something less than 360 degree rotation. A fixed tibial assembly generally refers to a tibial assembly wherein the tibial insert is not movable relative to the tibial tray and remains in a fixed location thereon. Surgeons may choose between fixed and mobile tibial assemblies depending upon the particular needs of the patient.

Typical mobile tibial assemblies fall into one of two classifications with respect to the insert-to-tray interface: unconstrained and constrained. In an unconstrained mobile tibial assembly, the tibial insert is free to move in all directions relative to the tibial tray. In a constrained mobile tibial assembly, the tibial insert is typically restricted from movement relative to the tibial tray in all but one or more directions and/or movements (e.g., translations and/or rotations).

SUMMARY

According to one aspect, a mobile tibial assembly may include a tibial tray and a tibial insert. The tibial tray may be configured to be coupled to a surgically-prepared surface of the proximal end of a tibia. Additionally, the tibial tray may include a closed track defined in an upper surface. The tibial insert may include a stem configured to be inserted into the closed track. Additionally, the tibial insert may be configured to move along the closed track while being retained therein.

The closed track may include a first end and a second end. At least one of the first end and the second end is closed. In some embodiments, the closed track may include an elongated opening defined in the upper surface of the tibial tray. In such embodiments, the stem of the tibial insert may have a dimension greater than the width of the opening. Additionally, the closed track may include an access opening, such as an elliptical, circular, rectangular, or polygonal opening, defined in the upper surface of the tibial tray. The access opening may be connected to the elongated opening. For example, the access opening may be positioned at one end of the elongated opening. The elliptical opening may have a dimension greater than the dimension of the stem. The closed track may be defined by a bottom wall, a first side wall, a second side wall, a first lip extending from the first side wall over a portion of the bottom wall, and a second lip extending from the second wall over a portion of the bottom wall. The first and second lips may define an opening therebetween. In some embodiments, each of the first and second lip may include a bottom surface substantially parallel to the bottom wall of the track. In other embodiments, each of the first and second lips may include a bottom surface oblique to the bottom wall of the track.

The stem of the tibial insert may be configured to be positioned in a first orientation that allows the stem to be inserted into the closed track and a second orientation that causes the stem to be retained in the closed track. The tibial insert may include a bottom surface and the stem may extend downwardly from the bottom surface. The stem may include a neck and a flange defined at an end of the neck. The flange may have dimension greater than a width of an opening of the closed track defined in the upper surface of the tibial tray. The flange may have an elliptical bottom profile, such as a circular bottom profile, when viewed in plan view. In some embodiments, the flange may also have a bottom surface substantially parallel to a the bottom surface of the tibial insert and an oblique top surface with respect to the bottom surface.

In other embodiments, the flange may have any one of a number of different bottom profile shapes when viewed in plan view. For example, the flange may have a rectangular bottom profile, a triangular bottom profile, a hexagonal or other polygonal or substantially polygonal bottom profile, or the like. In embodiments wherein the flange has a rectangular bottom profile, the flange may have a length greater than a width of an elongated opening of the closed track and a width less than the width of the elongated opening. The flange may include a first end and a second end extending from the neck of the stem. The first and second end may be curved in some embodiments. The second end may extend from the neck farther than the first end in some embodiments. In such embodiments, the closed track may be defined by a bottom wall, a first side wall, a second side wall, a first lip extending from the first side wall a first distance, and a second lip extending from the second wall a second distance greater than the first distance. The first and second lips may define an opening therebetween. The first lip may establish a region thereunder configured to receive a portion of the first end and the second lip may establish a region thereunder configured to receive a portion of the second end of the flange.

According to another aspect, a mobile tibial assembly may include a tibial tray and a tibial insert. The tibial tray may be configured to be coupled to a surgically-prepared surface of the proximal end of a tibia. Additionally, the tibial tray may include a closed track having an elongated opening defined in an upper surface. The tibial insert may include a bottom surface and a stem. The stem may extend downwardly from the bottom surface. The stem may include a flange defined at an end of a neck. The flange may have a dimension greater than a width of the elongated opening of the closed track.

The closed track may include an elliptical opening defined in the upper surface of the tibial tray at one end of the elongated opening. The elliptical opening may have a dimension greater than the dimension of the stem. The stem may be configured to be positioned in a first orientation that allows the stem to be inserted into the closed track and a second orientation that causes the stem to be retained in the closed track. The flange may have a circular bottom profile when viewed in plan view in some embodiments. Alternatively, the flange may have a rectangular bottom profile when viewed in plan view. The flange may include a first end and a second end extending from the stem. The second end may extend from the stem farther than the first end.

According to a further aspect, a method for implanting a tibial assembly may include securing a tibial tray to a surgically-prepared surface of the proximal end of a tibia. The tibial tray may include a closed track defined in an upper surface. The method may also include positioning a tibial insert in a first orientation. Additionally, the method may include inserting a stem of the tibial insert into the closed track while the tibial insert is in the first orientation. The method may also include moving the tibial insert to a second orientation to cause the tibial insert to be retrained in the closed track.

BRIEF DESCRIPTION OF THE DRAWINGS

The detailed description particularly refers to the following figures, in which.

DETAILED DESCRIPTION OF THE DRAWINGS

Figure 1:
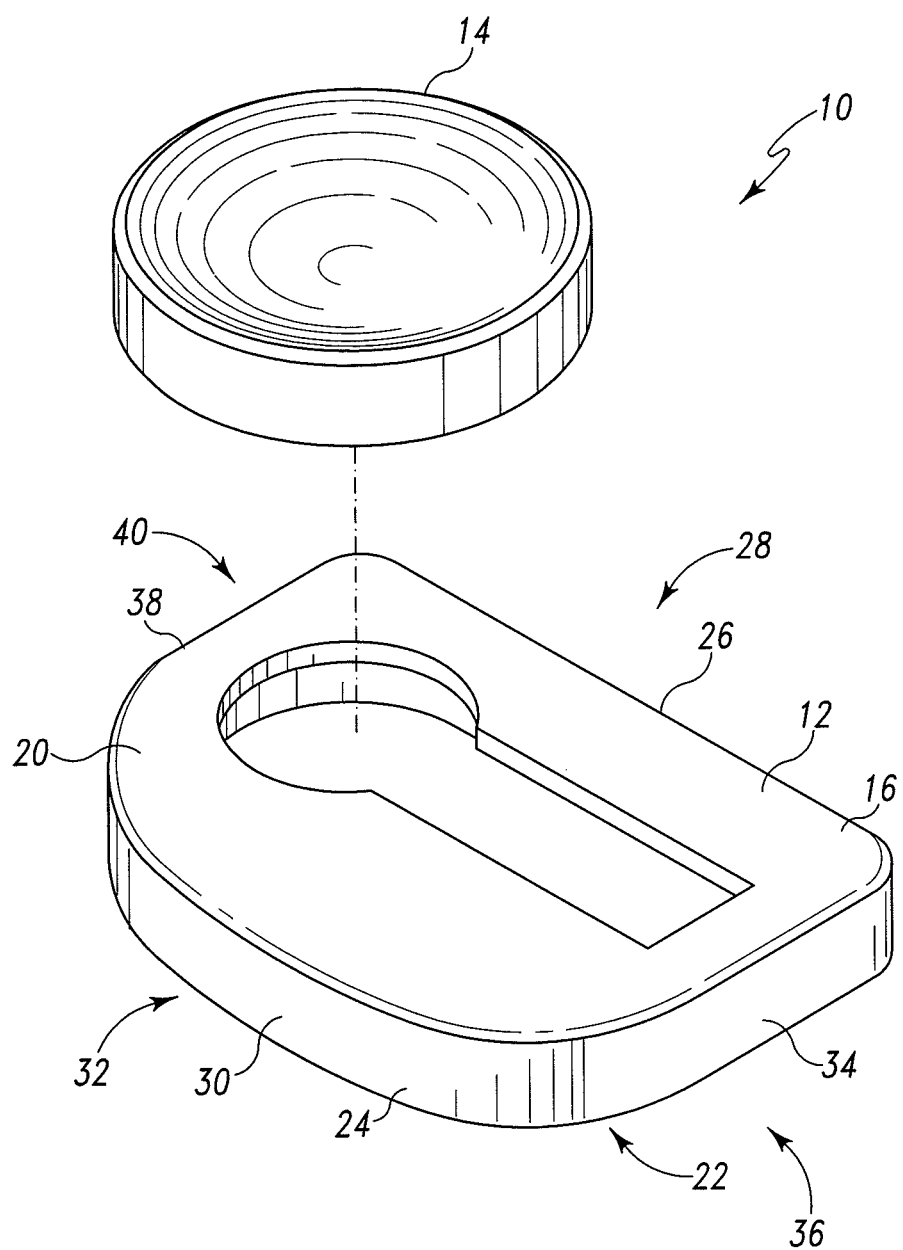
FIG. 1 is a perspective view of a unicompartmental mobile tibial assembly.
Figure 2:
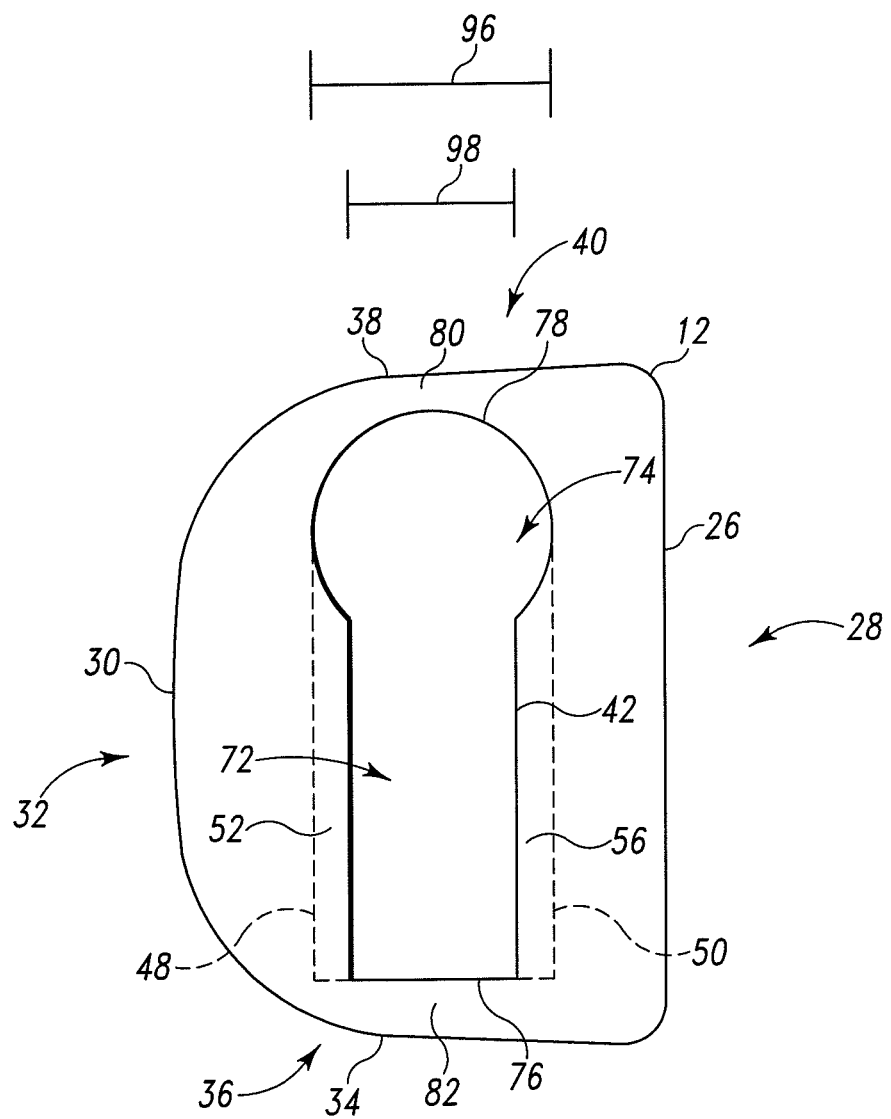
FIG. 2 is a plan view of the tibial tray of the unicompartmental mobile tibial assembly of FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

A number of different embodiments of tibial assemblies are described below. Illustratively, the tibial assemblies are illustrated and described as unicompartmental tibial assemblies intended to replace only one of the two bearing surfaces of a patient's tibia. As such, the tibial assemblies may be used by an orthopaedic surgeon or other healthcare provider during the performance of a unicompartmental knee arthroplasty (UKA) procedure. However, it should be appreciated that the tibial assemblies described herein may also be used during the performance of a total knee arthroplasty (TKA) procedure. For example, a single tibial assembly may be used for each bearing surface of the tibia thereby improving the overall customizability of the orthopaedic implant compared to typical total knee arthroplasty implants. Additionally, the tibial assemblies described herein may be used by the surgeon or other healthcare provider during the performance of an orthopaedic surgical procedure using either conventional or minimally invasive surgical methods. Further, although the features of the tibial assemblies are described in reference to an orthopaedic knee implant, it should be appreciated that such features are applicable to other types of orthopaedic implants including, but not limited to, hip implants, shoulder implants, elbow implants, spine implants, finger implants, toe implants, wrist implants, and ankle implants.

Referring now to FIGS. 1-7, in one embodiment, a tibial assembly 10 includes a tibial tray 12 and a bearing, herein referred to as tibial insert 14. The tibial insert 14 is illustratively formed from a polymer material, but may be formed from other materials, such as a ceramic material, a metallic material, a bio-engineered material, or the like, in other embodiments. Similarly, the tibial tray 12 is illustratively formed from a metallic material, but may be formed from other materials, such as a ceramic material, a polymer material, a bio-engineered material, or the like, in other embodiments.

The tibial tray 12 is configured to be coupled to a surgically-prepared surface of the proximal end of a patient's tibia (not shown) as described below. The tibial tray 12 includes a base 16 and a number of anchoring devices 18, commonly referred to as stems or keels, extending downwardly therefrom. When the tibial tray 12 is coupled to the patient's tibia, the anchoring devices 18 are embedded in the patient's tibia to thereby secure the tibial tray 12 to the patient's bone.

The base 16 has a generally "D"-shaped top profile and includes an upper surface 20 and a bottom surface 22 from which the anchoring devices 18 extend. The base 16 has a generally straight side surface 26 defining a inboard side 28 of the tibial tray, a generally curved side surface 30 defining an outboard side 32 of the tibial tray 12, an end surface 34 defining an anterior side 36 of the tibial tray 12, and an end surface 38 defining a posterior side 40 of the tibial tray 12. It should be appreciated that the illustrative tibial assembly 10 is but one embodiment of a tibial assembly and that the features and components of the tibial assembly 10 may be used with a tibial assembly configured to replace the medial and/or lateral condyle of a patient's right tibia, as well as, the medial and/or lateral condyle of the patient's left tibia.

Figure 4:
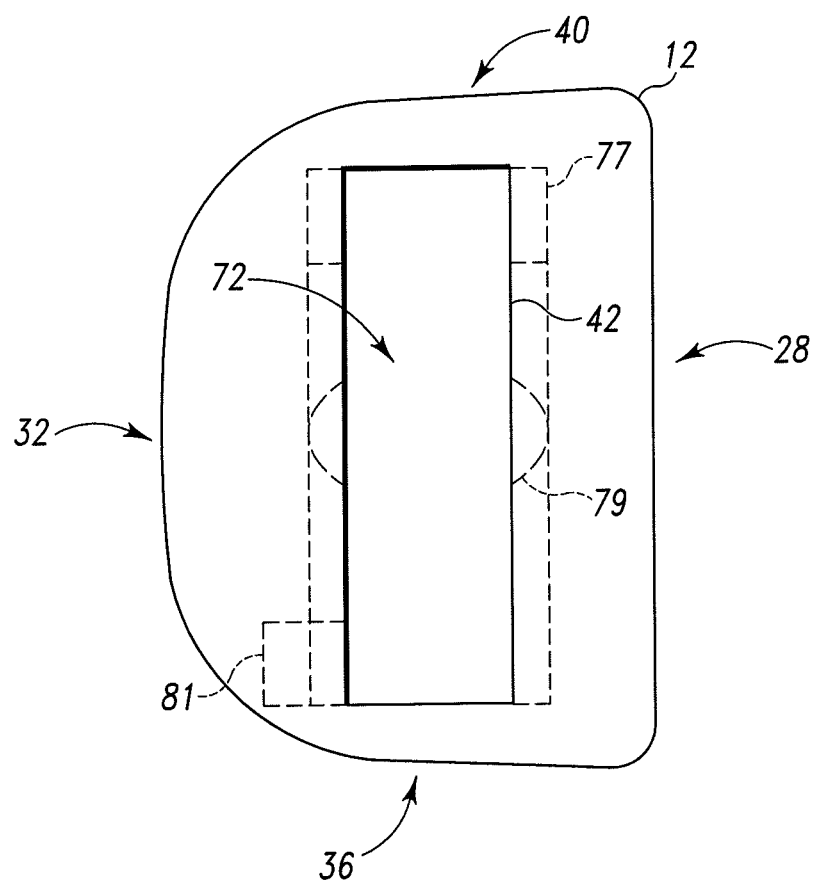
FIG. 4 is a plan view of another embodiment of the tibial tray of the unicompartmental mobile tibial assembly of FIG. 1.

The tibial tray 12 includes a track 42 defined in the base 16. As described below, the track 42 is configured to receive a stem 44 of the tibial insert 14 and retain a portion of the stem 44 therein while allowing the tibial insert 14 to move relative to the tibial tray 12. As shown in FIG. 4, the track 42 is defined by a bottom wall 46 and side walls 48, 50. An outboard lip 52 extends from the side wall 48 a distance 54. Similarly, a inboard lip 56 extends from the side wall 50 a distance 58. In the illustrative embodiment of FIG. 4, the lips 52, 56 extend from the side walls 48, 50, respectively, an equal distance (i.e., the distance 54 is substantially equal to the distance 58). However, in other embodiments, the lips 52, 56 may extend from the side walls 48, 50 different distances as discussed below in regard to FIGS. 13-15.

The illustrative walls 48, 50 have a substantially straight cross-sectional profile. However, in other embodiments, the walls 48, 50 may have other configurations. For example, the walls 48, 50 may be convex or concave in some embodiments. Additionally the walls 48, 50 may be angled or otherwise curved in other embodiments As such, it should be appreciated that the walls 48, 50 may have any cross-sectional profile shape configured to contact or be positioned adjacent to the corresponding walls of a stem of the tibial insert 14 as discussed in more detail below.

Figure 5:
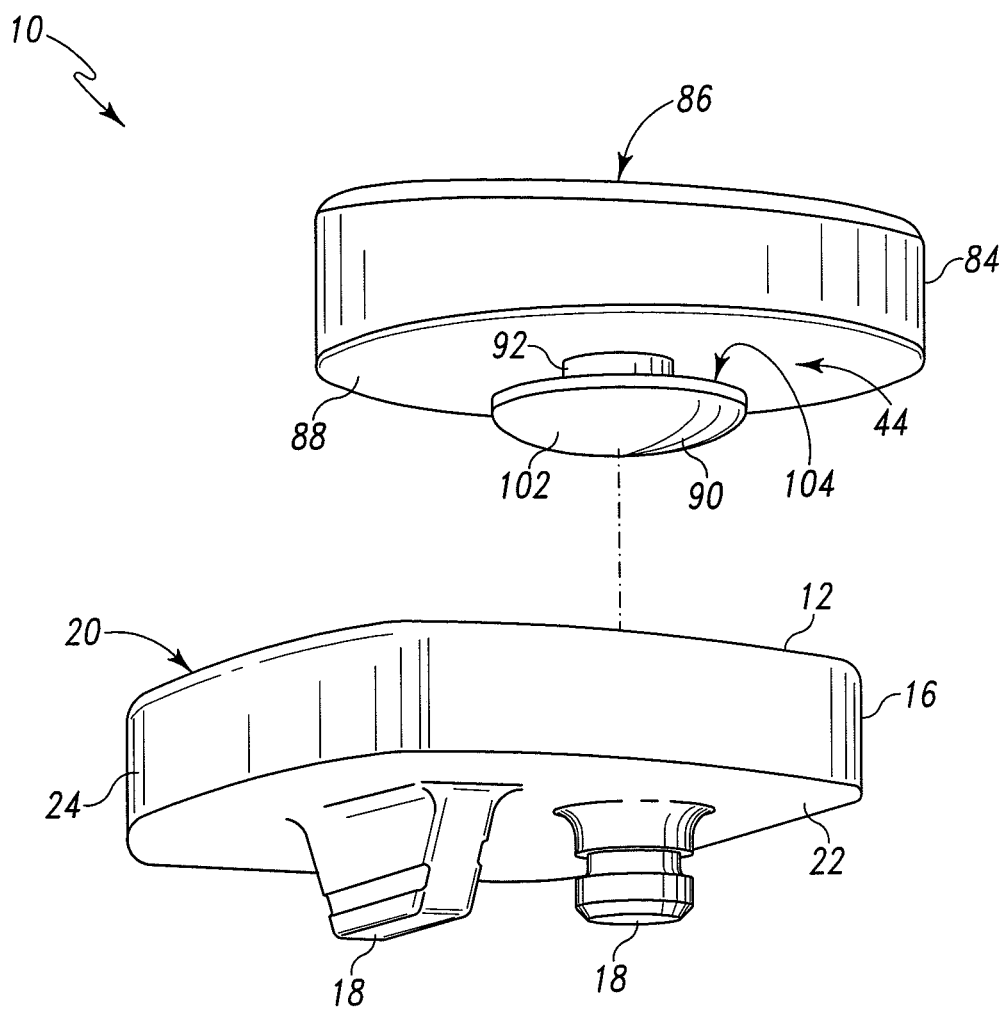
FIG. 5 is another perspective view of the unicompartmental mobile tibial assembly of FIG. 1.

The outboard lip 52 includes a top surface 60 and a bottom surface 62. Similarly, the inboard lip 56 includes a top surface 64 and a bottom surface 66. In the illustrative embodiment of FIG. 4, the top surface 60 of the lip 52 is substantially parallel to the bottom surface 62 of the lip 56. Similarly, the top surface 64 of the inboard lip 56 is substantially parallel to the bottom surface 66 of the second lip 56. However, in other embodiments, the top surfaces 60, 64 may not be parallel to the respective bottom surface 62, 66. For example, as illustrated in FIG. 5, the outboard lip 52 may include a bottom surface 68 that is oblique or otherwise non-parallel to the top surface 60. Similarly, the inboard lip 56 may include a bottom surface 70 that is oblique or otherwise non-parallel to the top surface 64. As discussed in more detail below, the particular angle between the top surfaces 60, 64 and respective bottom surfaces 68, 70 of the lips 52, 56 may be selected such that the track 42 is configured to accommodate different embodiments of the tibial insert 14.

Referring back to FIG. 2, the lips 52, 56 extend from the respective side walls 48, 50 so as to define an elongated opening 72 therebetween. The elongated opening 72 is defined in the upper surface 20 of the base 16 and extends longitudinally in a generally anterior-posterior direction. However, in other embodiments, the elongated opening 72 (i.e., the track 42) may be defined in the upper surface 20 in any orientation. That is, the elongated opening 72 may be defined in the upper surface 20 in a generally anterior-posterior direction, a generally medial-lateral direction, or some combination thereof (i.e., a generally diagonal direction). Additionally, although the illustrative elongated opening 72 is substantially straight, the tibial tray 12 may include an elongated opening having other configurations in other embodiments. For example, a curved elongated opening may be used in some embodiments.

Figure 3:
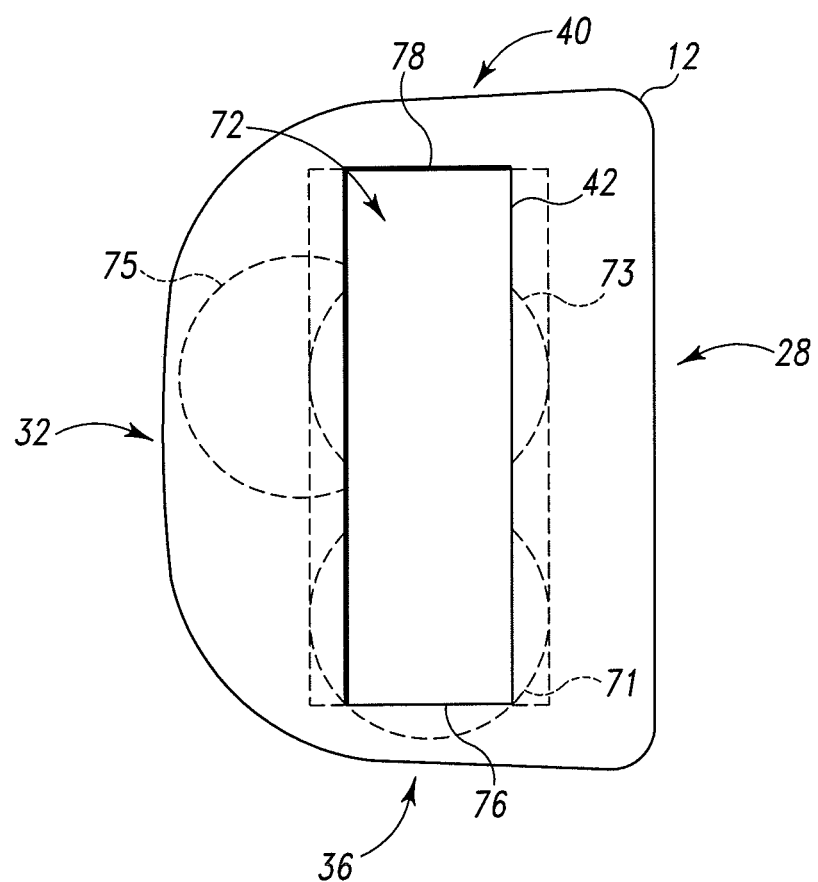
FIG. 3 is a plan view of another embodiment of the tibial tray of the unicompartmental mobile tibial assembly of FIG. 1.

The elongated opening 72 of the track 12 includes an access opening 74 defined at the posterior end 78 of the track 42. However, although the access opening 74 is illustratively defined at the posterior end 78 of the track 42 in FIG. 2, the access opening 74 may be defined at any position along the track 42 and/or offset from the track 42 in other embodiments. For example, as illustrated in FIG. 3, the access opening 74 may be embodied as an access opening 71 positioned at the anterior end 76 of the track 42, an access opening 73 positioned in a generally central location along the track 42 or otherwise away from the ends 76, 78, and/or as an access opening 75 offset from the track 42 but connected thereto.

As discussed in more detail below, the access opening 74 provides an aperture through which the stem 44 of the tibial insert 14 may be inserted into the track 42. As such, although the illustrative access opening 74 is embodied as an elliptical or circular opening, the access opening 74 may have other shapes in other embodiments based on, for example, the shape of the stem 44 of the tibial insert. For example, as illustrated in FIG. 4, in embodiments wherein the stem 44 has a substantially rectangular bottom profile shape, the access opening 74 may be embodied as an access opening 77 having a similar rectangular shape. Alternatively, in embodiments, wherein the stem 44 has a substantially oval or oblong bottom profile shape, the access opening 74 may be embodied as an access opening 79 having a similar oval or oblong shape. Further, as discussed above, the access opening 74 may be offset, but connected to, the track 42. For example, in embodiments wherein the stem 44 has a substantially rectangular bottom profile shape as discussed above, the access opening 74 may be embodied as a rectangular access opening 81 offset to one side of the track 42 so as to form a substantial "L" shape with the track 42. In such embodiments, the stem 44 of the tibial insert 14 may be inserted into the access opening 81 and subsequently moved into the track 42 such that the tibial insert 14 may move along the track 42 as discussed in more detail below. As such, it should be appreciated that the access opening 74 may have any shape that allows the stem 44 of the tibial insert 14 to be received therein and may be located on the top surface 20 of the base 16 in any position relative to, and in connection with, the track 42 (e.g., at any position along the track 42, offset from the track 42, etc.).

It should be appreciated that the track 42 is embodied as a closed track. That is, unlike an open track, one or both of the ends 76, 78 of the track 42 is not "open" and, as such, does not extend to the respective end surface 34, 38 of the base 16. Rather, an end wall 80 of the base 16 is defined between the end 78 of the track 42 and the end surface 38 and/or an end wall 82 is defined between the end 76 of the track 42 and the end surface 34. The ends walls 80, 82 may be of any thickness depending upon such factors as the length of the track 42, the particular orthopedic application of the assembly 10, and the like.

The tibial insert 14 includes a base 84 from which the stem 44 extends. The base 84 includes an upper bearing surface 86 and a bottom surface 88. The stem 44 extends downwardly from the bottom surface 88 of the base 84. The upper bearing surface 86 of the tibial insert 14 is configured to engage a natural or prosthetic femoral component of a patient's femur. During use, the patient's femur or femoral component articulates on the upper bearing surface 86.

Figure 6:
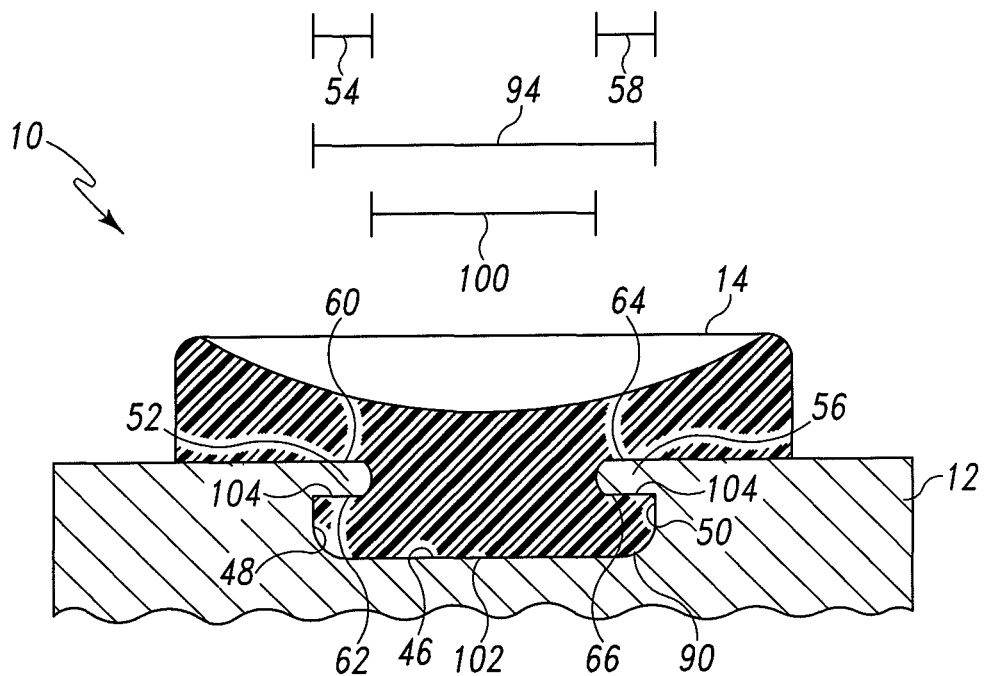
FIG. 6 is a cross-sectional view of the unicompartmental mobile tibial assembly of FIG. 1 having the tibial insert retained in the closed track of the tibial tray.

The stem 44 of the tibial insert 14 includes a flange 90 and a neck 92 connecting the flange 90 to the bottom surface 88 of the base 84. The flange 90 has a shape corresponding to the access opening 74 such that the flange 90 of the stem 44 may be inserted into the track 42 via the access opening 74. For example, in the illustrative embodiment of FIGS. 1-7, the flange 90 has a generally elliptical or circular bottom profile corresponding to the elliptical or circular shape of the access opening 74. However, in other embodiments, the flange 90 may have any one of a number of configurations configured to be received by the access opening 74 and the track 42. For example, the flange 90 may be rectangular, triangular, hexagonal or otherwise polygonal, or the like in other embodiments. As shown in FIG. 6, the illustrative flange 90 has a width or diameter 94 that is slightly less than the width or diameter 96 of the access opening 74 (see FIG. 2) such that the flange 90 may be inserted into the access opening 74. However, the diameter 94 of the flange 90 is greater than the width 98 of the elongated opening 42 defined by the lips 52, 56 of the track 42. The neck 92 has a width or diameter 100 that is slightly less than the width 98 of the elongated opening 42.

Figure 7:
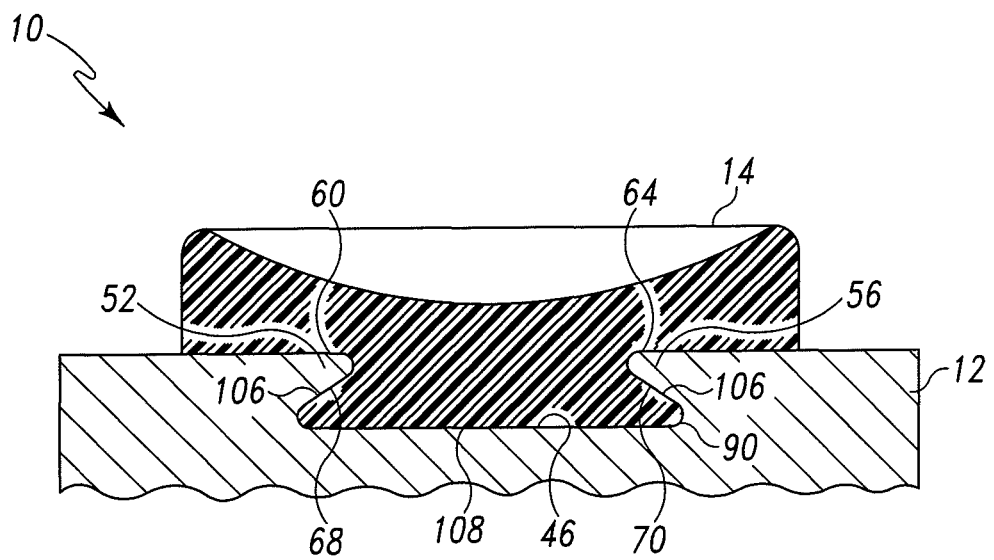
FIG. 7 is a cross-sectional view of another embodiment of a unicompartmental mobile tibial assembly.

The flange 90 includes an bottom surface 102 and an upper surface 104. In the embodiment illustrated in FIGS. 5 and 6, the bottom surface 102 is substantially parallel to the upper surface 104. Additionally, the bottom surface 102 and the upper surface 104 are substantially parallel to the bottom surface 46 of the track 42 when the tibial insert 14 is received therein. However, as shown in FIG. 7, the tibial insert 14 may include a flange 90 having an upper surface 106 that is oblique to or otherwise not parallel to the a bottom surface 108 of the flange 90. Additionally, in such embodiments, the upper surface 106 of the flange 90 is not parallel to the bottom surface 46 of the track 42 when the tibial insert 14 is received therein.

During the performance of the orthopaedic surgical procedure (e.g., a UKA or TKA procedure), the tibial insert 14 may be coupled to the tibial tray 12 by inserting the stem 44 of the tibial insert 14 into the track 42 of the tibial tray 12. To do so, the tibial insert 14 is positioned such that the flange 90 of the stem 44 is inserted into the access opening 74 of the track 42. Once the flange 90 is received by the access opening 74, the tibial insert 14 may be slid or otherwise moved toward the anterior side 36 of the base 16. Because the diameter 100 of the neck 92 of the stem 44 is less than the width 98 of the elongated opening 72, the tibial insert 14 may be moved along the elongated opening 72 of the track 42. Additionally, because the diameter 94 of the flange 90 is greater than the width 98 of the elongated opening 72, the lips 52, 56 retain the flange 90, and thereby the tibial insert 14, in the track 42. As such, the lips 52, 56 prevent the tibial insert 14 from lifting off the tibial tray 12.

As shown in FIG. 6, when the tibial insert 14 is received by the track 42, the bottom surface 102 of the flange 90 contacts or is otherwise adjacent to the bottom surface 46 of the track 42. Additionally, the upper surface 104 of the flange 90 contacts or is otherwise adjacent to the bottom surfaces 62, 66 of the lips 52, 56, respectively. Similarly, as shown in FIG. 7, in embodiments in which the top surface 106 of the flange 90 is oblique or otherwise not parallel to the bottom surface 108, the top surface 106 contacts or is otherwise adjacent to the bottom surfaces 68, 70 of the lips 52, 56, respectively.

During patient use, the tibial insert 14 moves back and forth along the track 42 of the tibial tray 12 in a generally anterior-posterior direction. In addition, in embodiments wherein the flange 90 has a substantially circular bottom profile, the tibial insert 14 may be configured to rotate about a center axis defined by the stem 44. As such, in use, the tibial insert 14 is configured to rotate while, or in addition to, moving generally anteriorly or posteriorly within the track 42. It should be appreciated that the access opening 74 is located on the base 16 in a manner such that the flange 90 does not exit the track 78 via the access opening 74 during normal use of the tibial assembly 10 by the patient. That is, the access opening 74 is positioned such that the tibial insert 14 is not moved to a position in which the flange 90 is substantially exposed to the access opening 74 during normal flexion and extension of the relevant knee joint of the patient.

Figure 8:
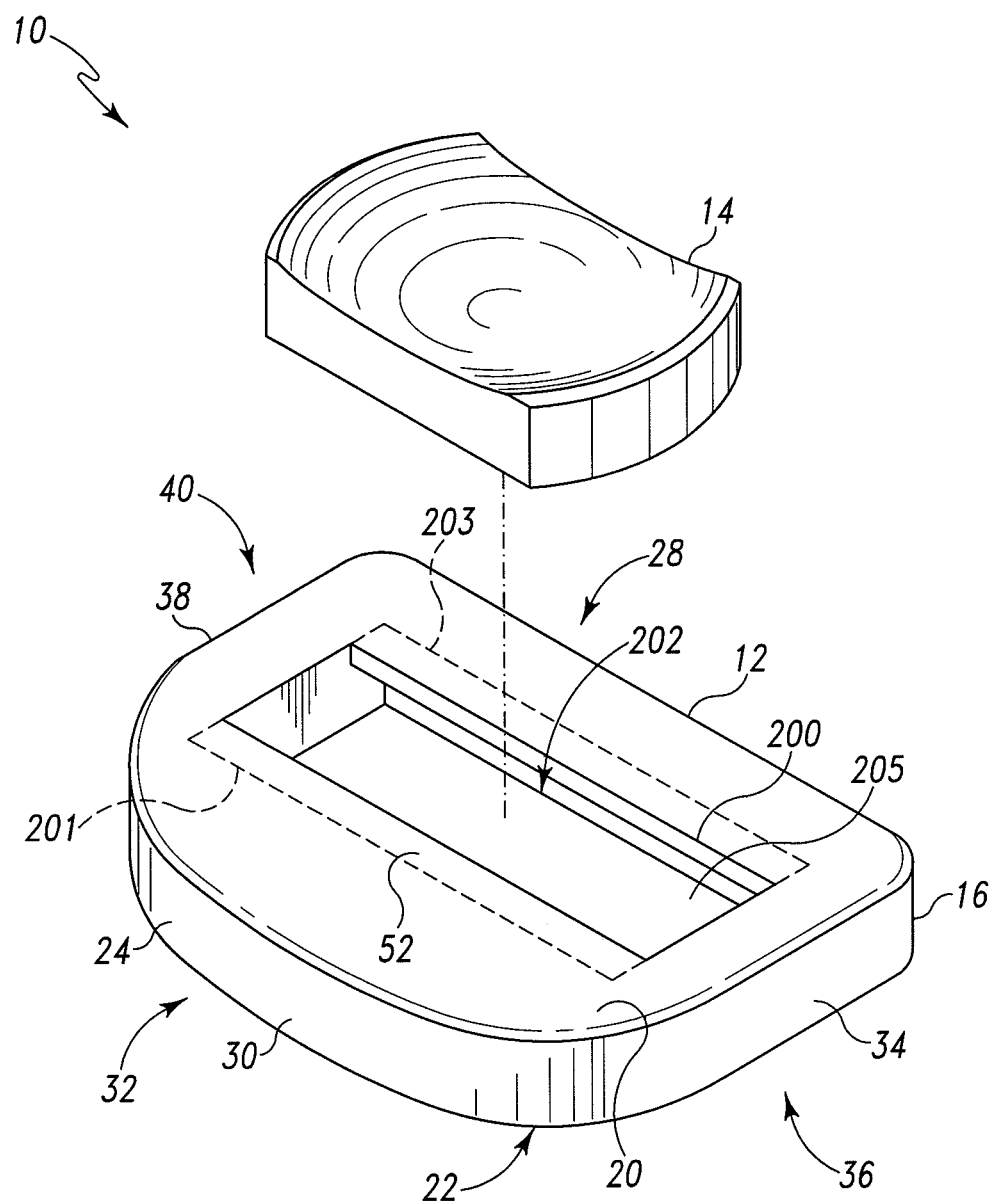
FIG. 8 is a perspective view of another embodiment of a unicompartmental mobile tibial assembly.
Figure 9:
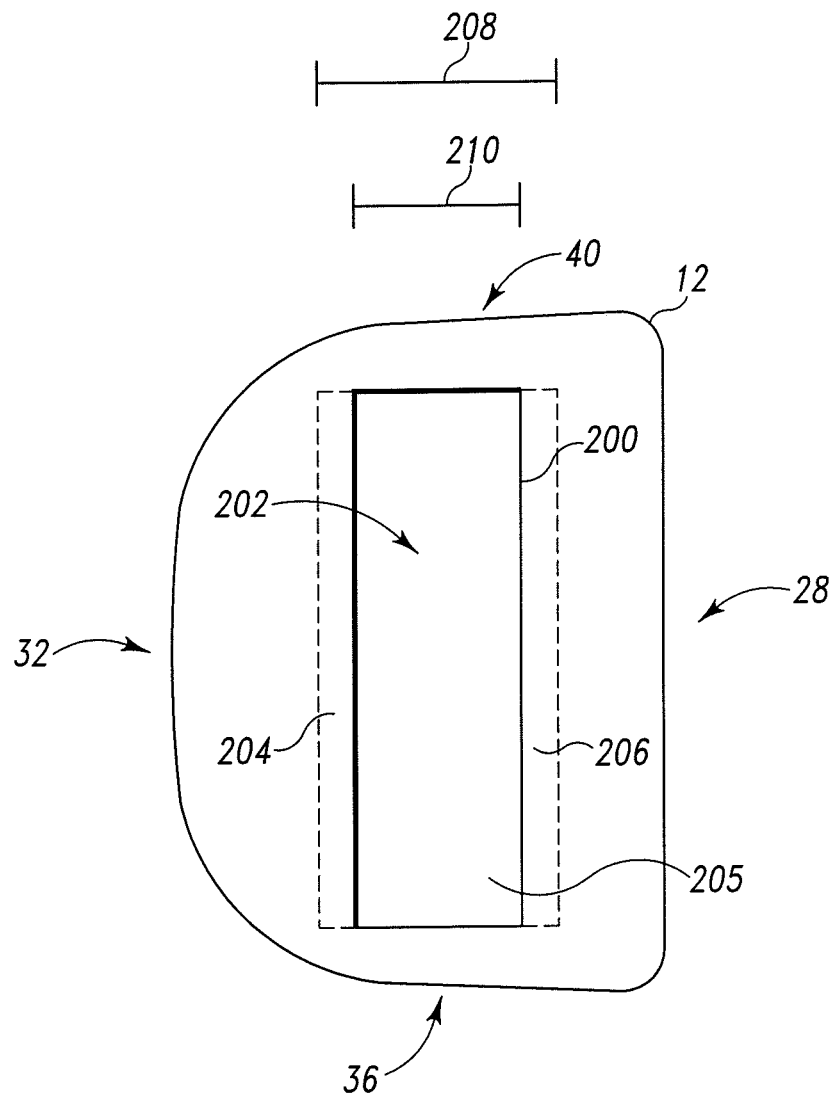
FIG. 9 is a plan view of the tibial tray of the unicompartmental mobile tibial assembly of FIG. 8.
Figure 10:
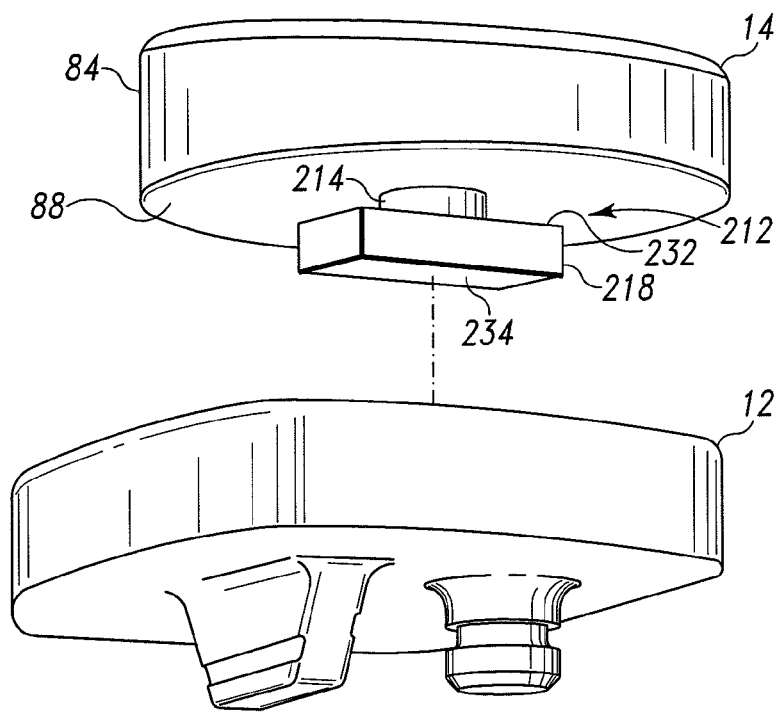
FIG. 10 is another perspective view of the unicompartmental mobile tibial assembly of FIG. 8.

Referring now to FIGS. 8-12, in another embodiment of the tibial assembly 10, the tibial tray 12 includes a track 200 in place of the track 42 described above. The track 200 is substantially similar to the track 42 and may, or may not, include the access opening 74. The track 200 includes an elongated opening 202, which is similar to elongated opening 72. As described above in regard to the track 42, the elongated opening 202 of the track 200 is bounded by lips 204, 206 extending from the side walls 201, 203 that define the track 200. As shown in FIG. 9, the track 200 has a width 208 defined by the distance between the side walls 201, 203 of the track 200. The elongated opening 72 has a width 210, which is less than the width 208 of the track 200.

As shown in FIG. 8, the illustrative tibial insert 14 has an oblong shape. However, tibial inserts having other shapes may be used in other embodiments. For example, the tibial insert 14 may have a circular shape as shown in FIG. 1. As such, it should be appreciated that the tibial assembly 10 may include a tibial insert 14 having any shape including, but not limited to, a circular shape, an oblong shape, an oval shape, or the like.

As illustrated in FIG. 9, in embodiments in which the tibial tray 12 includes the track 200, the tibial insert 14 includes a stem 112 extending downwardly from the bottom surface 88 of the base 84. The stem 112 includes a flange 218 and a neck 214 connecting the flange 218 to the bottom surface 88 of the base 84. The illustrative flange 218 has a generally rectangular bottom profile, but may have other shapes in other embodiments. For example, the flange 218 may have a rectangular bottom profile, a triangular bottom profile, a hexagonal or other polygonal or substantially polygonal bottom profile, or the like in other embodiments.

Figure 11:
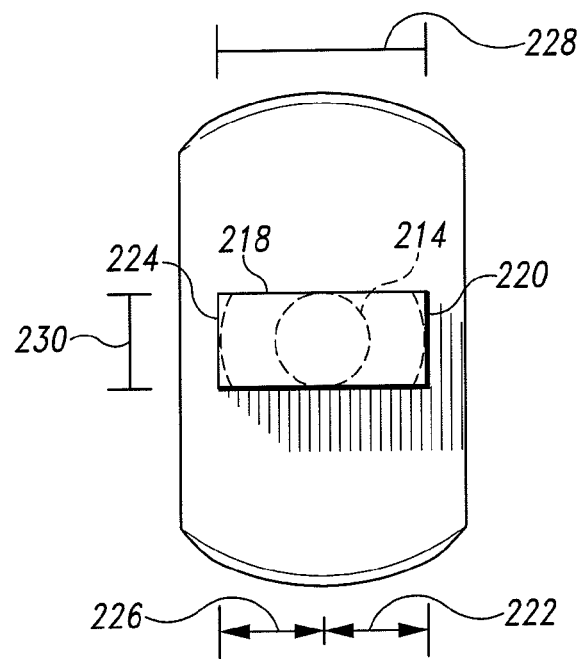
FIG. 11 is a bottom plan view of the tibial insert of the unicompartmental mobile tibial assembly of FIG. 8.

The flange 218 includes an end 220 extending from the neck 214 a distance 222 and an end 224 extending from the center of the neck 214 a distance 226. In the illustrative embodiment of FIGS. 8-12, the distances 222, 226 are substantially equal, but may be different in other embodiments as discussed below in regard to FIGS. 13-15. As shown in FIG. 11, the illustrative ends 220, 224 of the flange 218 are substantially straight. However, in other embodiments, the ends 220, 224 may be curved or otherwise not straight, as shown in phantom in FIG. 11, to improve the ease of inserting the tibial insert 14 into the track 200 as discussed below.

The flange 218 has a length 228 which is greater than its width 230. The flange 218 is configured such that the length 228 of the flange 218 is slightly smaller than the width 208 of the bottom wall 205 of the track 200 but greater than the width 210 of the elongated opening 202 of the track 200. Additionally, the width 230 of the flange 218 is slightly less than the width 210 of the elongated opening 202. As such, the flange 218 includes dimensions (i.e., the length 228 and width 230) that allow the flange 218 of the stem 44 to be inserted into the track 200 in a longitudinal orientation as discussed in more detail below.

The flange 218 includes an upper surface 232 and a bottom surface 234. In the embodiment illustrated in FIGS. 8-112, the upper surface 232 is substantially parallel to the bottom surface 234. Additionally, the upper surface 232 and the bottom surface 234 are substantially parallel to the bottom surface 205 of the track 200 when the tibial insert 14 is received therein. However, in other embodiments, the surfaces 232, 234 of the tibial insert 14 may not be parallel to each other. In such embodiments, the lips 204, 206 of the track 200 may also include oblique or otherwise non-parallel bottom surfaces similar to the bottoms surfaces 68, 70 of the lips 52, 56 as illustrated in and described above in regard to FIG. 7.

Figure 12:
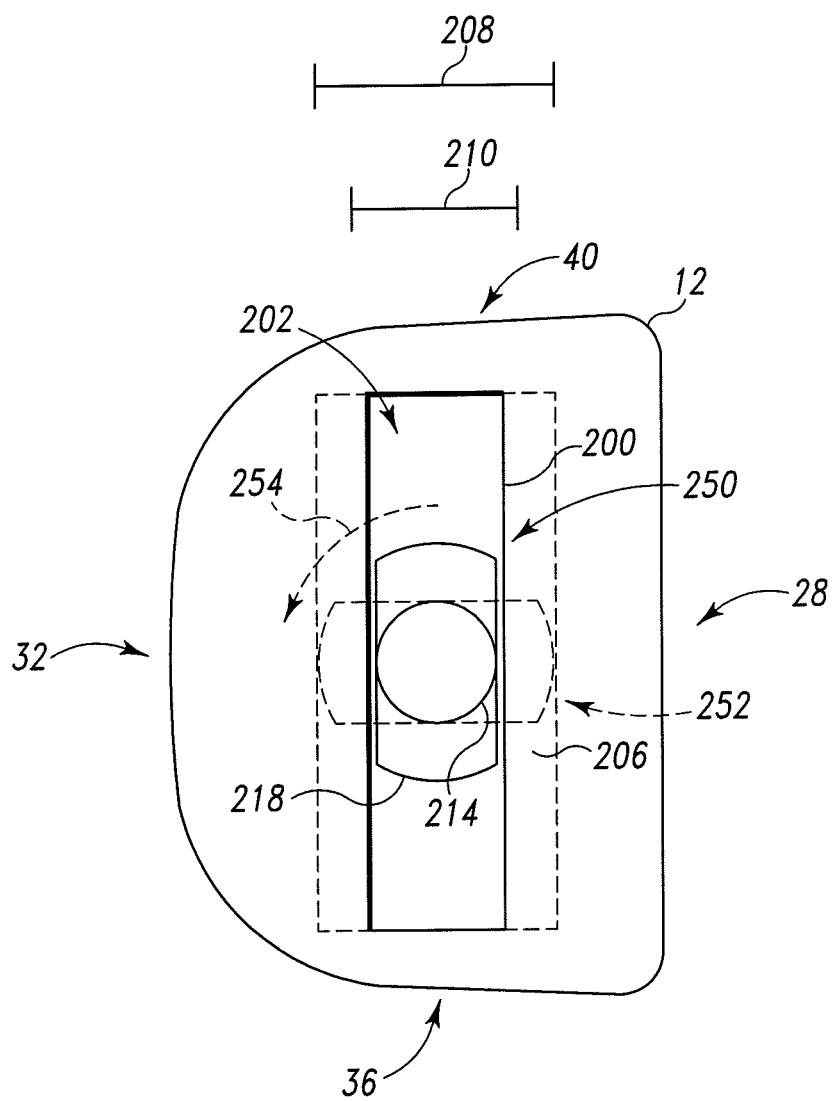
FIG. 12 is a plan view of the unicompartmental mobile tibial assembly of FIG. 8 in an assembled configuration and having a base of the tibial insert removed for clarity.

During the performance of the orthopaedic surgical procedure (e.g., a UKA or TKA procedure), the tibial insert 14 may be coupled to the tibial tray 12 by inserting the stem 212 of the tibial insert 14 into the track 200 of the tibial tray 12. To do so, as shown in FIG. 12, the tibial insert 14 is positioned in an initial orientation 250 such that the flange 218 is in registry with the elongated opening 202. For example, as shown in FIG. 12, in embodiments in which the elongated opening 202 is defined in the upper surface 20 of the tibial tray 12 in a generally anterior-posterior direction, the tibial insert 14 may be positioned in a similar anterior-posterior direction (i.e.,initial orientation 250) with respect to the tibial insert 12. Because the width 230 of the flange 218 (see FIG. 9) is slightly less than the width of the elongated opening 202, the flange 218 of the stem 212 may be inserted into track 200.

Once the flange 218 has been inserted into the track 200 via the elongated opening 202, the tibial insert 12 is turned in a generally rotational direction as indicated by arrow 254 or otherwise moved to another orientation 252 such that the flange 218 is substantially orthogonal with respect to the elongated opening 202. In the illustrative embodiment of FIG. 12, the ends 220, 224 are curved or generally rounded to thereby allow or otherwise increase the ease with which the tibial insert 14 may be moved to the retained orientation 252 (i.e., the ends 220, 224 are not restricted by the track's walls 201, 203). Because the length 228 of the flange 218 is greater than the width 210 of the elongated opening 202, the flange 218 is retained in the track 200 via the lips 204, 206, which define the elongated opening 202 when in the retrained orientation 252. As such, the lips 204, 206 prevent the tibial insert 14 from lifting off the tibial tray 12. Additionally, as with the stem 44, because the diameter of the neck 214 of the stem 212 is less than the width 210 of the elongated opening 202, the tibial insert 14 may be moved along the elongated opening 202 of the tibial tray 12 while being retained in the track 200.

If desired, the tibial insert 14 may be removed from the tibial tray 12 by reversing the above-described procedure. That is, the tibial insert 14 may be de-coupled from the tibial tray 12 by turning or otherwise moving the tibial insert 14 into the initial position such that the flange 212 is in registry with the elongated opening 202 of the track 200. Once so positioned, the tibial insert 14 may be removed from the track 200 by lifting the tibial insert 14 off of the tibial tray 14.

Figure 13:
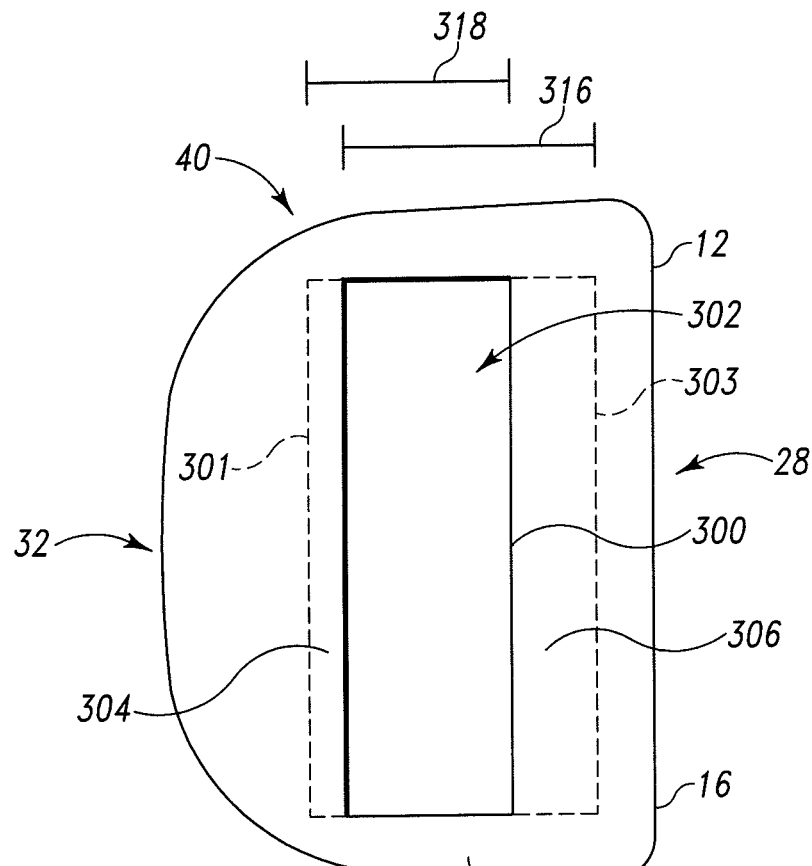
FIG. 13 is a plan view of another embodiment of the tibial tray of the unicompartmental mobile tibial assembly of FIG. 8.

During patient use, the tibial insert 14 moves along the track 200 of the tibial tray 12 in a generally anterior-posterior direction. In addition, in embodiments wherein the length 228 of the flange 218 is sufficiently smaller than the width 208 of the track's bottom wall 205 and the width of the neck 214 is sufficiently smaller than the width 210 of the elongated opening 202, the tibial tray 12 may be configured to move some amount in a generally medial-lateral direction while, or in addition to, moving in a generally anterior-posterior direction Referring now to FIGS. 13-15, in another embodiment of the tibial assembly 10, the tibial tray 12 includes a track 300 in place of the track 42. The track 300 is substantially similar to the track 200 described above in regard to FIGS. 6-9 and includes an elongated opening 302 defined on the top surface 20 of the tibial tray 14. As described above in regard to the track 42, the elongated opening 302 of the track 300 is defined by a pair of lips 304, 306 extending from the sidewalls 301, 303 that define the track 300. However, unlike the track 200 described above in regard to FIGS. 8-12, the lips 304, 306 extend from the sidewalls 301, 303 different distances. That is, as illustrated in FIG. 13, the outboard lip 304 extends from the sidewall 301 a distance 308 and the inboard lip 306 extends from the sidewall 303 a distance 310. The distance 310 is greater than the distance 308 such that the cross-sectional area 312 defined under the inboard lip 306 is greater than the cross-section area 314 defined under the outboard lip 304. As such, the track's bottom wall 346 has a width 316 defined by the distance between the side walls 301, 303 that is greater than the width 318 of the elongated opening 302, but is offset relative to the opening 302 as shown in FIG. 13.

Figure 14:
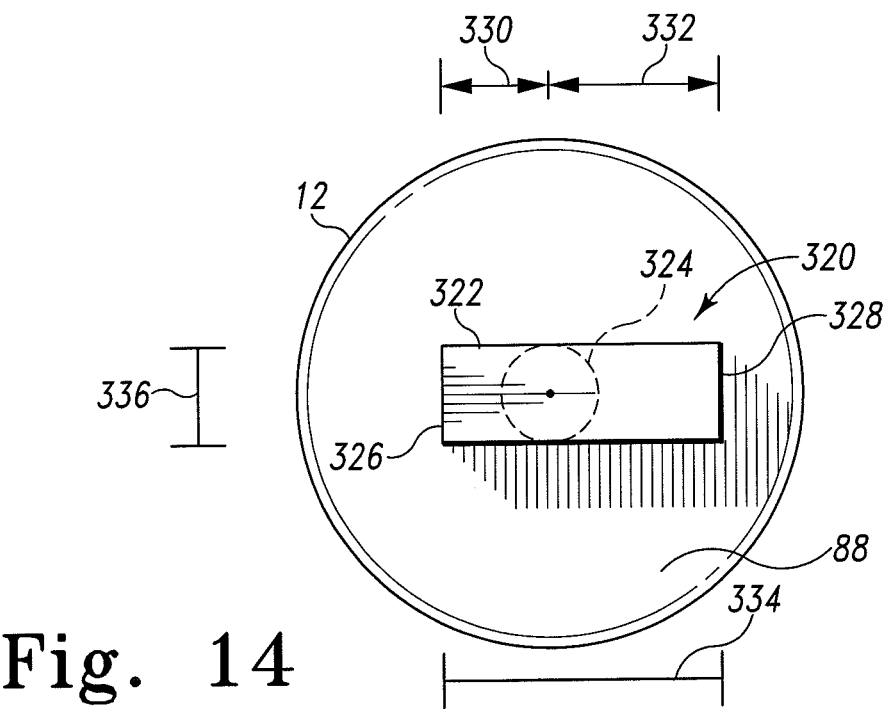
FIG. 14 is a bottom plan view of another embodiment of a tibial insert for use with the tibial tray illustrated in FIG. 13.

As illustrated in FIG. 14, in embodiments in which the tibial tray 12 includes the track 300, the tibial insert 14 includes a stem 320 extending downwardly from the bottom surface 88. The stem 320 includes a flange 322 and a neck 324 connecting the flange 322 to the bottom surface 88 of the tibial insert 14. Similar to the flange 220 described above in regard to FIGS. 8-12, the flange 322 has a generally rectangular bottom profile. Again, however, the flange 322 may have other shapes in other embodiments. For example, the flange 322 may have a rectangular bottom profile, a triangular bottom profile, a hexagonal or other polygonal or substantially polygonal bottom profile, or the like in other embodiments.

Similar to flange 220, the flange 322 includes ends 326, 328. However, in the embodiment illustrated in FIGS. 13-15, the end 328 extends from the neck 324 farther than the end 326. That is, the shorter end 326 extends from the neck 324 a distance 222 and the longer end 328 extends from the neck 324 a distance 332, which is greater than the distance 222. Again, as shown in FIG. 14, the illustrative ends 326, 328 are substantially straight, but may be curved or otherwise not straight in other embodiments similar to the flange 220 illustrated in FIG. 11.

The flange 322 has a length 334 which is greater than its width 360. The flange 322 is configured such that the length 334 of the flange 322 is slightly smaller than the width 316 of the track's bottom wall 346 but greater than the width 318 of the elongated opening 302 of the track 300. Additionally, the width 336 of the flange 322 is slightly less than the width 318 of the elongated opening 302. As such, the flange 322 includes dimensions (i.e., the length 334 and width 336) that allows the flange 322 of the stem 320 to be inserted into the track 300 in a longitudinal orientation as discussed in more detail below.

Figure 15:
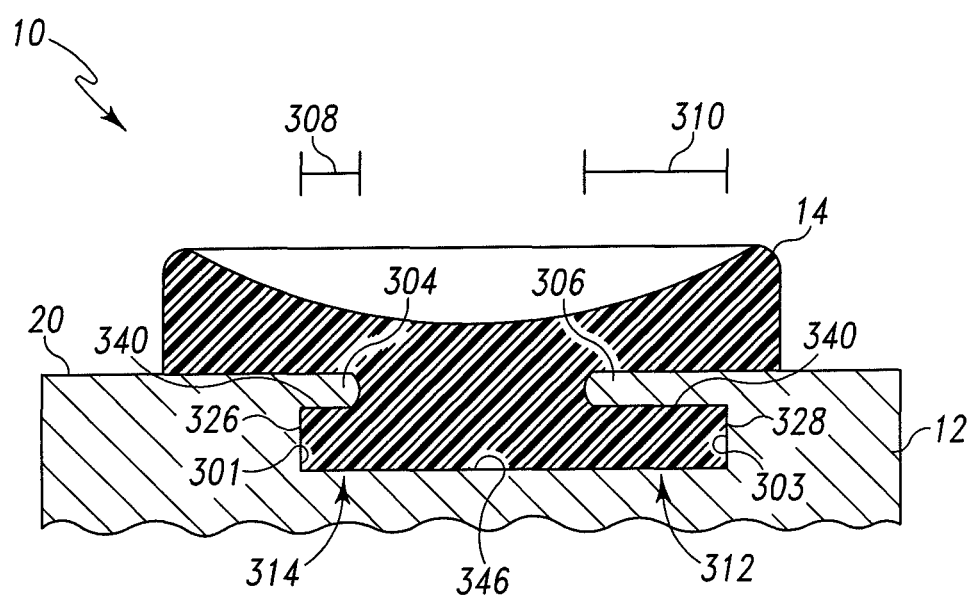
FIG. 15 is a is a cross-sectional view of the tibial insert of FIG. 14 being retained in the closed track of the tibial tray of FIG. 13.

As shown in FIG. 15, the flange 322 includes an upper surface 340 and a bottom surface 342. In the embodiment illustrated in FIGS. 13-15, the upper surface 340 is substantially parallel to the bottom surface 342. Additionally, the upper surface 340 and the bottom surface 342 are substantially parallel to the bottom wall 346 of the track 300 when the tibial insert 14 is received therein. However, in other embodiments, the surfaces 340, 342 of the tibial insert 14 may not be parallel to each other. In such embodiments, the lips 304, 306 of the track 300 may also include oblique or otherwise non-parallel bottom surfaces similar to the bottoms surfaces 68, 70 of the lips 52, 56 as illustrated in and described above in regard to FIG. 7.

During the performance of the orthopaedic surgical procedure (e.g., a UKA or TKA procedure), the tibial insert 14 may be coupled to the tibial tray 12 by inserting the stem 320 of the tibial insert 14 into the track 300 of the tibial tray 12 in a similar manner as described above in regard to FIG. 12. To do so, the tibial insert 14 is positioned in an initial orientation such that the flange 320 is in registry with the elongated opening 302 (i.e., similar to orientation 250 shown in FIG. 12). For example, in the illustrative embodiment of FIG. 13 wherein the elongated opening 304 is defined in the upper surface 20 of the tibial tray 12 in a generally anterior-posterior direction, the tibial insert 14 may be positioned in a similar anterior-posterior direction with respect to the tibial tray 12. Because the width 336 of the flange 322 is slightly less than the width of the elongated opening 318, the flange 322 of the stem 320 may be inserted into track 200.

Once the flange 322 has been inserted into the track 300 via the elongated opening 302, the tibial insert 12 is turned or otherwise moved to another orientation such that the flange 322 is substantially orthogonal with respect to the elongated opening 302 (i.e., similar to orientation 252 shown in FIG. 12). However, because the end 328 extends from the neck 324 a distance greater than the end 326, the tibial insert 14 may only be turned to the orientation wherein the longer end 328 is received in the larger cross-sectional area 312 defined under the lip 306 of the track 300. If, however, the tibial insert 14 is turned in the opposite direction, the longer end 328 is configured to contact the sidewall 301 of the track 300 prior to reaching a latitudinal orientation. In this way, the configuration of the track 300 and the flange 322 ensure that the tibial insert 14 may be coupled to the tibial tray 12 in only a single orientation. That is, the flange 322 of the tibial insert 14 may only be received by the track 300 in an orientation wherein the shorter end 326 is positioned adjacent the sidewall 301 and the longer end 328 is positioned adjacent the sidewall 303. As such, the likelihood of misaligning tibial trays having asymmetric features is reduced.

Because the length 334 of the flange 322 is greater than the width 318 of the elongated opening 302, the flange 332 is retained in the track 300 via the lips 304, 306, which define the elongated opening 302. As such, the lips 304, 306 prevent the tibial insert 14 from lifting off the tibial tray 12. Additionally, as with the stem 44, because the diameter of the neck 324 of the stem 320 is less than the width 318 of the elongated opening 302, the tibial insert 14 may be moved along the elongated opening 302 of the track 300 while being retained therein. If desired, the tibial insert 14 may be removed from the tibial tray 12 by reversing the above-described procedure. That is, the tibial insert 14 may be de-coupled from the tibial tray 12 by turning or otherwise moving the tibial insert 14 into the initial position such that the flange 322 is in registry with the elongated opening 302 of the track 300. Once so positioned, the tibial insert 14 may be removed from the track 300 by lifting the tibial insert 14 off of the tibial tray 14.

During patient use, the tibial insert 14 moves along the track 300 of the tibial tray 12 in a generally anterior-posterior direction. In addition, in embodiments wherein the length 334 of the flange 322 is sufficiently smaller than the width 316 of the track's bottom wall 346 and the width of the neck 324 is sufficiently smaller than the width 318 of the elongated opening 302, the tibial tray 12 may be configured to move some amount in a generally medial-lateral direction while, or in addition to, moving in a generally anterior-posterior direction.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and methods described herein. It will be noted that alternative embodiments of the devices and methods of the present disclosure may not include all of the features described yet still benefit from at least some of the advantages of such features. Those of ordinary skill in the art may readily devise their own implementations of the devices and methods that incorporate one or more of the features of the present invention and fall within the spirit and scope of the present disclosure as defined by the appended claims.

The invention claimed is:
1. A mobile tibial assembly comprising:
a monolithic tibial tray configured to be coupled to a surgically-prepared surface of the proximal end of a tibia, the tibial tray having a closed track having an elongated opening defined in an upper surface, the elongated opening having a length extending in an anterior-posterior direction and a width extending in a medial-lateral direction, the length being greater than the width of the elongated opening; and a tibial insert having a bottom surface and a stem extending downwardly from the bottom surface, the stem having a neck extending through the elongated opening and a flange defined at an end of the neck configured to be received in the closed track, the flange having (i) a first dimension greater than the width of the elongated opening of the closed track, (ii) a second dimension less than the first dimension and less than the width of the elongated opening of the closed track and extending transverse to the first dimension, and (iii) a concave bearing surface configured to engage a femoral prosthetic component, the bearing surface having a surface width and a surface length that is greater than the surface width, wherein the tibial insert is engaged with the tibial tray and is rotatable between a plurality of orientations relative to the tibial tray while engaged with the tibial tray, the plurality of orientations including: (i) a first orientation in which the first dimension of the flange and the surface width of the bearing surface are orthogonal to the width of the elongated opening and the second dimension of the flange and the surface length of the bearing surface are parallel to the width of the elongated opening such that the flange is permitted to be received in the closed track, and (ii) a second orientation in which the first dimension of the flange and the surface width of the bearing surface are parallel to the width of the elongated opening such that the flange is retained in the closed track.

2. The mobile tibial assembly of claim 1, wherein the closed track comprises an access opening defined in the upper surface of the tibial tray and connected to the elongated opening, the access opening having a dimension greater than the dimension of the stem.

3. The mobile tibial assembly of claim 1, wherein the flange includes a first end and a second end extending from the neck, the first and second end being curved.

4. The mobile tibial assembly of claim 3, wherein the flange includes a first end and a second end extending from the neck, the second end extending from the neck farther than the first end.

5. A mobile tibial assembly comprising:

a monolithic tibial tray configured to be coupled to a surgically-prepared surface of the proximal end of a tibia, the tibial tray having a closed track, the closed track comprising an elongated opening defined in an upper surface of the tibial tray, the elongated opening having a length extending in an anterior-posterior direction and a width extending in a medial-lateral direction, the length being greater than the width of the elongated opening; and a tibial insert including (i) a stem extending through the elongated opening defined in the upper surface of the tibial tray and received in the closed track, (ii) a flange extending from an end of the stem, the flange having a first dimension that is greater than the width of the elongated opening of the closed track and a second dimension that is less than the first dimension, less than the width of the elongated opening of the closed track, and extends transverse to the first dimension, and (iii) a concave bearing surface that has a surface width and a surface length that is greater than the surface width, wherein the tibial insert is engaged with the tibial tray and is moveable between a plurality of orientations relative to the tibial tray while engaged with the tibial tray, the plurality of orientations including (i) a first orientation in which the first dimension of the flange and the surface width of the bearing surface are parallel to the length of the elongated opening of the closed track to permit the stem to be removed from the closed track, and (ii) a second orientation in which the first dimension of the flange and the surface width of the bearing surface are orthogonal to the length of the elongated opening to retain the stem in the closed track and to prevent the tibial insert from being separated from the tibial tray, and wherein the tibial insert is configured to move along the length of the elongated opening in the anterior-posterior direction while being retained in the closed track.

6. The mobile tibial assembly of claim 5, wherein the closed track comprises a first end and a second end, the first and second ends being closed.

7. The mobile tibial assembly of claim 5, wherein the closed track comprises a first end and a second end, only one of the first end and the second end being opened.

8. The mobile tibial assembly of claim 5, wherein the stem of the tibial insert has a dimension greater than the width of the elongated opening.

9. The mobile tibial assembly of claim 8, wherein the closed track comprises an access opening defined in the upper surface of the tibial tray and connected to the elongated opening, the access opening having a dimension greater than the dimension of the stem.

10. The mobile tibial assembly of claim 9, wherein the access opening is defined at an end of the elongated opening.

11. The mobile tibial assembly of claim 9, wherein the access opening is defined in the upper surface of the tibial tray offset from the elongated opening.

12. The mobile tibial assembly of claim 5, wherein the closed track is defined by a bottom wall, a first side wall, a second side wall, a first lip extending from the first side wall over a portion of the bottom wall, and a second lip extending from the second wall over a portion of the bottom wall, the first and second lips defining the elongated opening therebetween.

13. The mobile tibial assembly of claim 12, wherein each of the first and second lips includes a bottom surface substantially parallel to the bottom wall.

14. The mobile tibial assembly of claim 12, wherein each of the first and second lips includes a bottom surface oblique to the bottom wall.

15. The mobile tibial assembly of claim 5, wherein the tibial insert comprises a bottom surface, the stem comprising:
a neck extending downwardly from the bottom surface, the neck being configured to extend through the elongated opening defined in the upper surface of the tibial tray, and
the flange is defined at an end of the neck.

16. The mobile tibial assembly of claim 15, wherein the flange has a bottom surface substantially parallel to the bottom surface of the tibial insert and an oblique top surface with respect to the bottom surface of the tibial insert.

17. The mobile tibial assembly of claim 15, wherein the flange comprises a first end and a second end, the first and second ends being curved.

18. The mobile tibial assembly of claim 15, wherein:
the flange has a rectangular bottom profile when viewed in plan view, and
the flange has a length greater than the width of the elongated opening and a width less than the width of the elongated opening.

19. The mobile tibial assembly of claim 15, wherein the flange is rectangular and includes a first end and a second end extending from the neck of the stem, the second end extending from the neck farther than the first end.

20. The mobile tibial assembly of claim 19, wherein the closed track is defined by a bottom wall, a first side wall, a second side wall, a first lip extending from the first side wall a first distance, and a second lip extending from the second wall a second distance greater than the first distance, the first and second lips define an opening therebetween.

21. The mobile tibial assembly of claim 20, wherein the first lip establishes a region thereunder configured to receive the first end of the flange and the second lip establishes a second region thereunder configured to receive the second end of the flange.

* * * * *